(12) United States Patent
Kashani et al.

(10) Patent No.: US 10,898,649 B2
(45) Date of Patent: Jan. 26, 2021

(54) SYRINGE (71) Applicant: NOVARTIS AG, Basel (CH)

(72) Inventors: Pooria Sharif Kashani, Irvine, CA (US); Omeed Paydar, Irvine, CA (US)

(73) Assignee: Alcon Inc., Fribourg (CH)

( * ) Notice: Subject to any disclaimer, the term of this patent is extended or adjusted under 35 U.S.C. 154(b) by 281 days.

(21) Appl. No.: 15/966,657

(22) Filed: Apr. 30, 2018

(65) Prior Publication Data
US 2018/0318517 A1 Nov. 8, 2018

Related U.S. Application Data (60) Provisional application No. 62/501,840, filed on May 5, 2017.

(51) Int. Cl.
*A61M 5/315* (2006.01)
*A61M 5/31* (2006.01)
*A61M 5/19* (2006.01)

(52) U.S. Cl.
CPC .......... *A61M 5/31513* (2013.01); *A61M 5/19* (2013.01); *A61M 5/3135* (2013.01); *A61M 5/31511* (2013.01); *A61M 5/31515* (2013.01); *A61M 2005/3128* (2013.01)

(58) Field of Classification Search
CPC .. A61M 5/19; A61M 5/3135; A61M 5/31511; A61M 5/31513; A61M 5/31515; A61M 2005/3128
See application file for complete search history.

(56) References Cited

U.S. PATENT DOCUMENTS

| | | | |
|---|---|---|---|
| 4,091,812 A | 5/1978 | Helixon |
| 4,643,724 A | 2/1987 | Jobe |
| 4,657,534 A | 4/1987 | Beck |
| 5,393,301 A | 2/1995 | Goldberg |
| 6,712,793 B1 | 3/2004 | Geiger et al. |
| 7,601,140 B2 | 10/2009 | Rossback |
| 9,220,631 B2 | 12/2015 | Sigg |

(Continued)

FOREIGN PATENT DOCUMENTS

EP  1166809 A1  1/2002

OTHER PUBLICATIONS

Module 5: Using Auto-Disable Syringes. Handbook [online]. Path, publication date unknown [retrieved on May 22, 2018]. Retrieved from <https://www.path.org/publicationsifiles/SafeIn/PDF-Module5.pdf>.

(Continued)

*Primary Examiner* — Manuel A Mendez
*Assistant Examiner* — Justin L Zamory (57) ABSTRACT

In a general aspect, a syringe terminates the dispensing of a fluid based on a force applied to a plunger member of the syringe. In some aspects, a plunger member of a syringe includes a top portion, a bottom portion, and a contact portion. The top and bottom portions are in contact with the contact portion, and the bottom portion has a length greater than or equal to a length of the top portion. The contact portion permits the top portion to move independent of the bottom portion in response to a stress in the contact portion exceeding a critical stress. The stress in the contact portion is based on a first force applied to the top portion and a second force opposite the first force applied to the bottom portion.

19 Claims, 8 Drawing Sheets

(56) References Cited

U.S. PATENT DOCUMENTS

| | | |
|---|---|---|
| 9,987,163 B2 | 6/2018 | Schaller |
| 10,182,906 B2 | 1/2019 | Auld |
| 10,434,010 B2 | 10/2019 | Auld |
| 2004/0199113 A1 | 10/2004 | Capes et al. |
| 2007/0185458 A1* | 8/2007 | Lin Lee .............. A61M 5/3234 604/197 |
| 2008/0097390 A1 | 4/2008 | Dacquay |
| 2008/0125712 A1 | 5/2008 | Dacquay |
| 2009/0177182 A1 | 7/2009 | Hickingbotham |
| 2009/0308386 A1* | 12/2009 | Kronestedt ....... A61M 15/0076 128/203.15 |
| 2012/0226240 A1 | 9/2012 | Bedford |
| 2014/0012227 A1 | 1/2014 | Sigg et al. |
| 2015/0105734 A1 | 4/2015 | Bryant et al. |
| 2019/0307962 A1 | 10/2019 | Latham |
| 2020/0016334 A1 | 1/2020 | Kashani |

OTHER PUBLICATIONS

K1 Auto Disable Information Film. YouTube [online] [video]. Uploaded Feb. 4, 2008 by user "Asstarsyringe" [retrieved Jun. 1, 2018]. Retrieved from <https://www.youtube.com/watch?v=jmsyuPUS-EM>.

* cited by examiner

SYRINGE

BACKGROUND

The following description relates to a syringe.

A syringe may include a plunger member and a barrel member. The syringe may be used to dispense a fluid stored in the barrel member of the syringe. The fluid may be dispensed by applying pressure to the plunger member of the syringe. In typical syringes, the fluid may be dispensed regardless of the amount of force applied to the plunger member.

SUMMARY

In a general aspect, a syringe terminates the dispensing of a fluid based on a force applied to a plunger member of the syringe.

In some aspects, a syringe includes a barrel member and a plunger member. The barrel member defines an inner chamber, and the plunger member is sized to fit within the barrel member, and includes a contact portion, a top portion, and a bottom portion. The top portion includes a first end and a second end opposite the first end. The first end of the top portion is adapted to receive a first force co-axial with the barrel member during operation, and the second end of the top portion is in contact with the contact portion. The bottom portion includes a first end and a second end opposite the first end, and has a length greater than or equal to a length of the top portion. The first end of the bottom portion in contact with the contact portion, and the second end of the bottom portion divides the inner chamber into a first inner volume portion and a second inner volume portion. The contact portion permits the top portion to move independent of the bottom portion in response to a stress in the contact portion exceeding a critical stress. The stress in the contact portion is based on the first force applied to the first end of the top portion and a second force opposite the first force, the second force applied to the second end of the bottom portion by a fluid in the second inner volume portion of the inner chamber.

In some aspects, a syringe plunger includes a contact portion, a first portion, and a second portion. The first portion includes a first end and a second end opposite the first end, with the second end of the first portion in contact with the contact portion. The second portion includes a first end and a second end opposite the first end, and has a length greater than or equal to a length of the first portion. The first end of the second portion is in contact with the contact portion. The contact portion permits the first portion to move independent of the second portion in response to a stress in the contact portion exceeding a critical stress. The stress in the contact portion is based on a first force applied to the first end of the first portion and a second force opposite the first force applied to the second end of the second portion.

In some aspects, a method of operating a syringe includes receiving a first force at a top portion of a plunger member. The top portion is in contact with a contact portion of the plunger member, and the first force is co-axial with a barrel member of the syringe. The method also includes receiving a second force at a bottom portion of the plunger member, which is in contact with the contact portion and disposed within the barrel member. The second force is opposite the first force and caused by a fluid in the barrel member in response to the first force. The method further includes permitting the top portion to move independent of the bottom portion in response to a stress in the contact portion exceeding a critical stress. The stress in the contact portion is caused by the first force and the second force.

The details of one or more implementations are set forth in the accompanying drawings and the description below. Other features, objects, and advantages will be apparent from the description and drawings, and from the claims.

DETAILED DESCRIPTION

In some aspects of what is described here, a syringe terminates the dispensing of a fluid when a stress induced in a portion of a plunger member exceeds a critical stress. For instance, the syringe may allow a first portion of the plunger member (e.g., a portion interacted with by an operator) to move independently of a second portion (e.g., a portion that is in contact with a fluid inside the barrel member of the syringe) when a force differential between a force applied to the plunger member and an opposing force (e.g., a force caused by the fluid inside the barrel member) exceeds a threshold. In some aspects, for example, a plunger member of the syringe includes a contact portion that is in contact with a top and bottom portion of the plunger member. The contact portion is configured to allow the top portion of the plunger member to move independently of the bottom portion of the plunger member when a stress in the contact portion (caused by the opposing forces) exceeds a critical stress.

For instance, in some implementations, a contact portion between top and bottom portions of a plunger member may experience a stress (e.g., tension or compression) when a force is applied to the top portion of the plunger member by an operator to dispense a fluid from the barrel member. When the force is applied to the top portion, an opposing force is applied to the bottom portion of the plunger member due at least partially to the viscosity of the fluid, inducing a stress in the contact portion. When this stress exceeds a critical stress (e.g., a yield strength of the contact portion), the contact portion may mechanically fail (e.g., sever, split, tear, or rupture). When this occurs, the contact portion allows the top portion of the plunger member to move independently of the bottom portion, preventing the force applied to the top portion from being transferred to the bottom portion and preventing any further dispensing of the fluid inside the barrel member of the syringe. For example, in some instances, after the contact portion has mechanically failed, an end of the top portion of the plunger member may extend into the barrel member of the syringe. The length of the bottom portion may be longer than the length of the top portion to prevent the top portion from transferring force to the bottom portion after the contact portion has mechanically failed.

Aspects of what is described here may provide certain advantages. In some aspects, for example, the syringe may prevent the dispensing of a fluid when a force needed to dispense the fluid becomes too great. For example, the syringe may be used in an ophthalmologic surgical procedure where a polymer adhesive material cures inside the barrel member of the syringe during the surgical procedure. When the polymer has substantially cured, it may be unsafe to further dispense the polymer material in the surgical procedure. A syringe according to the present disclosure may prevent dispensing of the polymer once it has cured to a certain critical point, since the force required to further dispense the material would cause a stress in the plunger member that exceeds a critical stress (which may be determined based on properties of the polymer material, e.g., the viscosity at which the polymer material becomes unsafe to further dispense during the procedure).

Figure 1A:
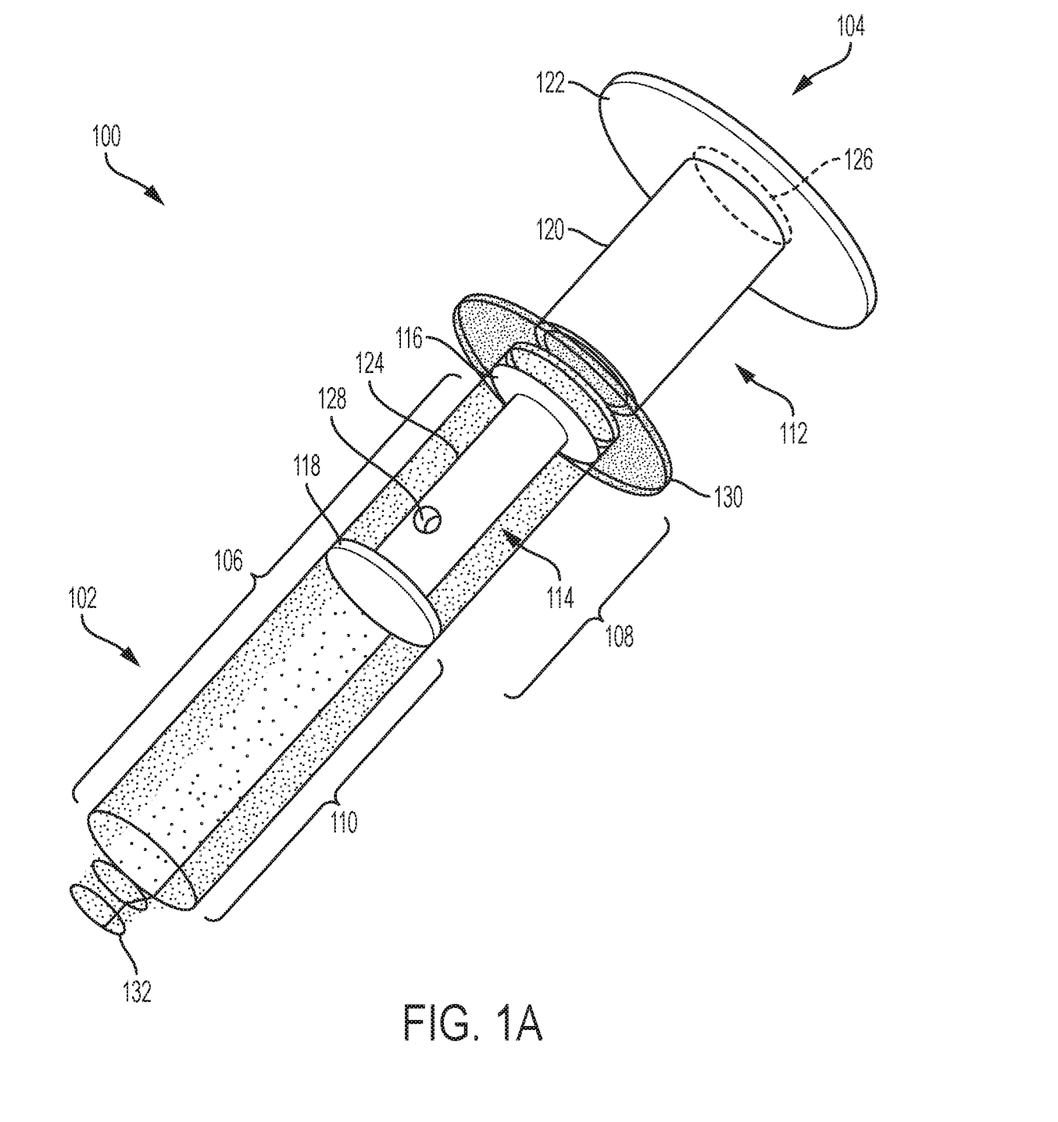
FIGS. 1A-1B are diagrams showing perspective and side views, respectively, of an example syringe.
Figure 1B:
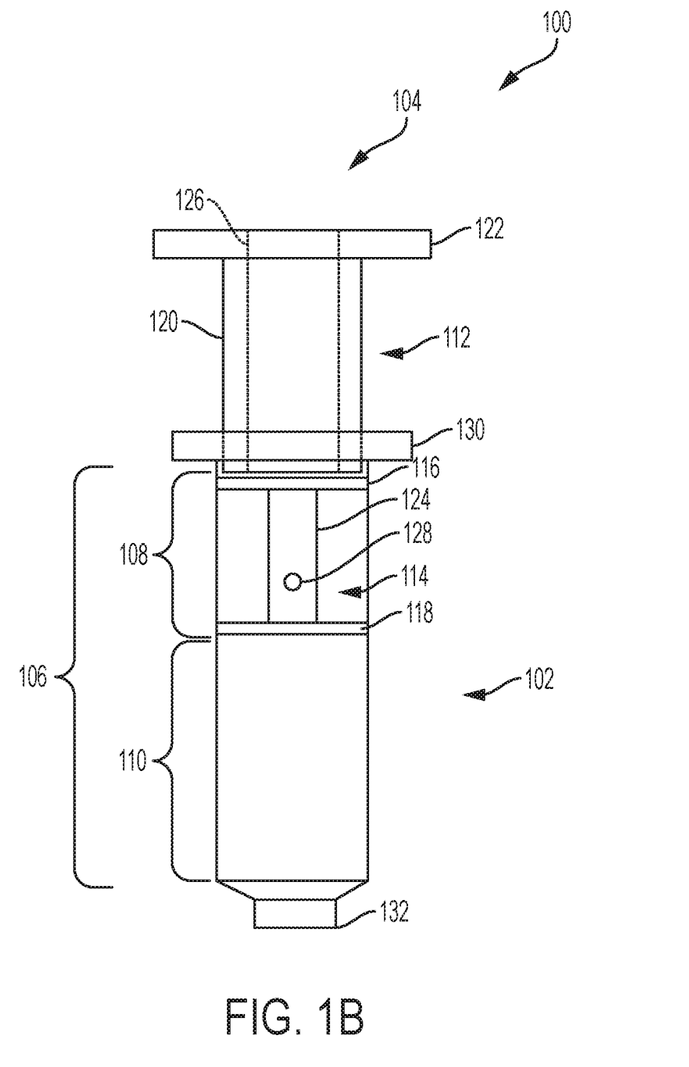

FIGS. 1A-1B are diagrams showing perspective and side views, respectively, of an example syringe 100. The syringe 100 includes a barrel member 102 and a plunger member 104. The barrel member 102 defines an inner chamber 106, a barrel flange 130 at a first end, and an outlet 132 at a second end opposite the first end. The plunger member 104 (with the exception of the plunger flange 122) is sized to fit within barrel member 102 (e.g., inside the inner chamber 106). When the plunger member 104 is at least partially disposed within the inner chamber 106 as shown in the example views of FIGS. 1A-1B, the inner chamber 106 is divided into a first inner volume portion 108 and a second inner volume portion 110. In some instances, the second inner volume portion 110 may be filled with a fluid for dispensing. For example, a polymer material (e.g., a two-part polymer system that includes a solid portion (e.g., polyethylene glycol (PEG)) and a liquid portion (e.g., PEG-amine and water) that cure when mixed together) may be placed inside the second inner volume portion 110 for dispensing during an ophthalmologic surgical procedure, or another type of fluid may be placed in the second inner volume portion 110. Each of the barrel member 102 and the plunger member 104 may be composed of any suitable material, such as, for example, polypropylene, polyethelene, glass, or another type of material. In some instances, portions of the barrel member 102 (e.g., the walls of the inner chamber 106) are coated with a silicone lubricant.

The plunger member 104 of the example syringe 100 includes a top portion 112, a bottom portion 114, and a contact portion 116 adapted to be in contact with each of the top portion 112 and the bottom portion 114. In the example shown in FIG. 1A (and also in FIGS. 3A-3B and described further below), the contact portion 116 is integral with the bottom portion 114. In some implementations, the contact portion 116 is integral with the top portion 112 (e.g., as shown in FIGS. 3C-3D and described further below). In some implementations, the top portion 112, bottom portion 114, and the contact portion 116 are distinct and not integral with one another (e.g., as shown in FIGS. 3E-3F and described further below). The contact portion 116 may be composed of the same materials as the top and bottom portions 112, 114 (e.g., polypropylene), or may be composed of another suitable material (e.g., polyethelene, hard rubber, or another material).

In the example shown, the top portion 112 includes a plunger flange 122 at a first end. The plunger flange 122 is adapted to receive a force during operation of the syringe 100. A second end of the top portion 112 (opposite the first end) is in contact with the contact portion 116. During normal operation, the first end of the top portion 112 may receive a force (e.g., via the plunger flange 122) that is co-axial or substantially co-axial with the barrel member 102 and the plunger member 104, causing the plunger member 104 to move further into the inner chamber 106, and dispensing a fluid in the second inner volume portion 110 from the outlet 132 of the barrel member 102. In the example shown, a first end of the bottom portion 114 is integral with the contact portion 116, and a second end of the bottom portion 114 (opposite the first end) includes a seal 118 that divides the inner chamber 106 into the first inner volume portion 108 and the second inner volume portion 110. The seal 118 may be any suitable material, such as, for example, a latex-free elastomer, polyethylene, polypropylene, or another type of material. The seal 118 may prevent fluid flow between the first inner volume portion 108 and the second inner volume portion 110.

Figure 4A:
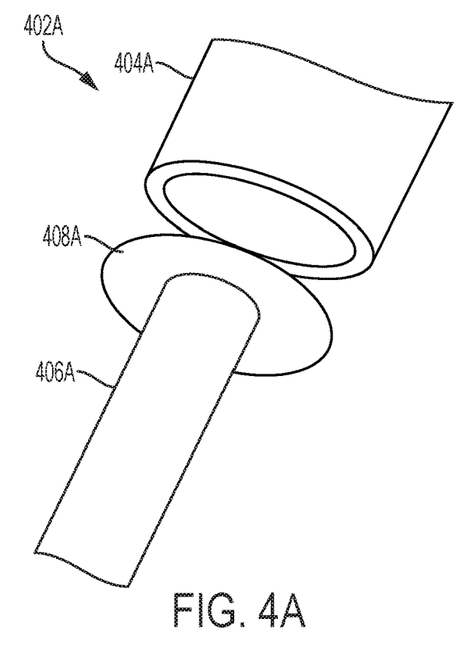
FIGS. 4A-4C are diagrams showing perspective views of example contact portion configurations for plunger members.
Figure 4B:
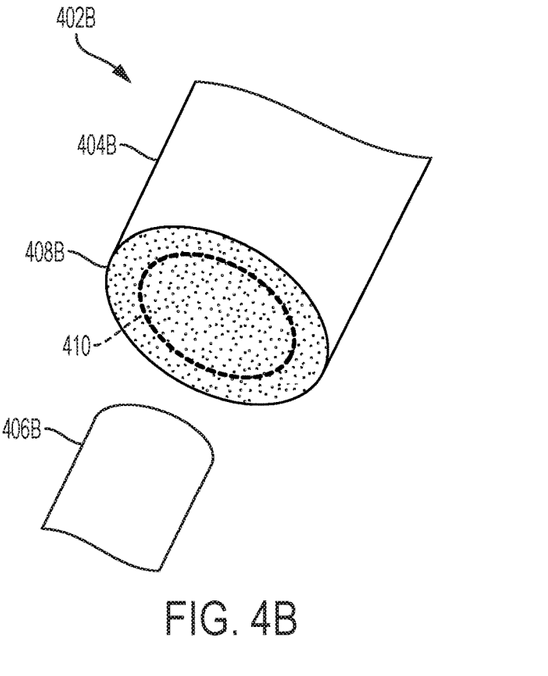
Figure 4C:
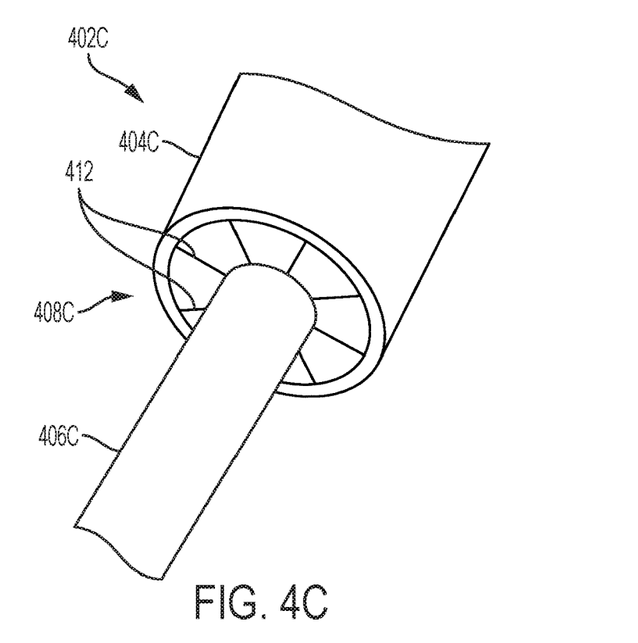

In some implementations, the contact portion 116 is designed to mechanically fail (e.g., sever, split, tear, or rupture) at a critical stress. The critical stress may be a pre-determined amount of stress that is based on the application of the syringe (e.g., which material is to be placed in the syringe for dispensing, the materials the syringe is composed of, etc.). For example, the contact portion 116 may be a membrane designed to mechanically fail at a critical stress that is based on a viscosity of a fluid in the syringe (e.g., a polymer curing in the syringe, and becoming more viscous over time). In the example shown in FIG. 1A, the contact portion 116 is a solid membrane (e.g., as also shown in FIG. 4A and described further below). In some instances, the critical stress is between one (1) and one thousand (1000) Newtons (N), such as, for example ten (10) Newtons (N), fifty (50) Newtons (N), one hundred (100) Newtons (N), or five hundred (500) Newtons (N). In some implementations, the contact portion 116 includes perforations (e.g., as shown in FIG. 4B and described further below). In some implementations, the contact portion 116 includes connecting members coupled between the top portion and the bottom portion (e.g., as shown in FIG. 4C and described further below). The contact portion 116 may be implemented in other ways.

The contact portion 116 may be designed to fail upon experiencing a particular force applied to the top portion 112 (the stress induced in the contact portion 116 is based on the force applied to the top portion 112). For instance, in some implementations, the contact portion 116 is designed with a particular thickness based on the yield strength of the constituent material. As an example, where the contact portion 116 is composed of WESTLAKE PLASTICS PROPYLUX polypropylene having a tensile yield strength of approximately 5310 pounds per square inch (psi), and the contact portion 116 comprises perforations (similar to the contact portion illustrated in FIG. 4B), the contact portion 116 may be designed to have a thickness of approximately 0.335 millimeters (mm) such that the contact portion 116 mechanically fails when experiencing a force of approximately ten (10) Newtons (N) at the top portion 112. Using the same example, the contact portion 116 may be designed to have a thickness of approximately 1.05 millimeters (mm) such that the contact portion 116 mechanically fails when experiencing a force of approximately one hundred (100) Newtons (N) at the top portion 112.

Figure 2A:
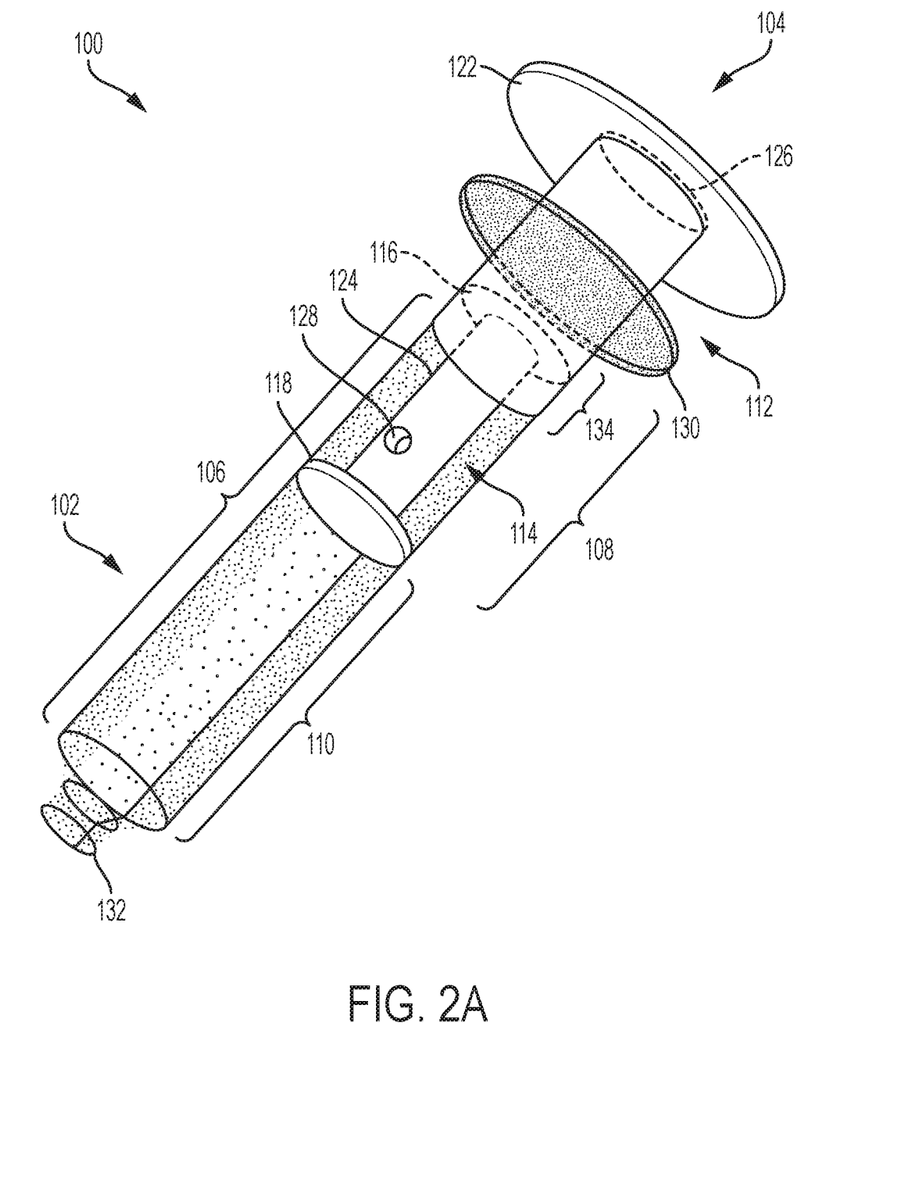
FIGS. 2A-2B are diagrams showing perspective and side views, respectively, of the example syringe of FIGS. 1A-1B after mechanical failure in the contact portion of the plunger member.
Figure 2B:
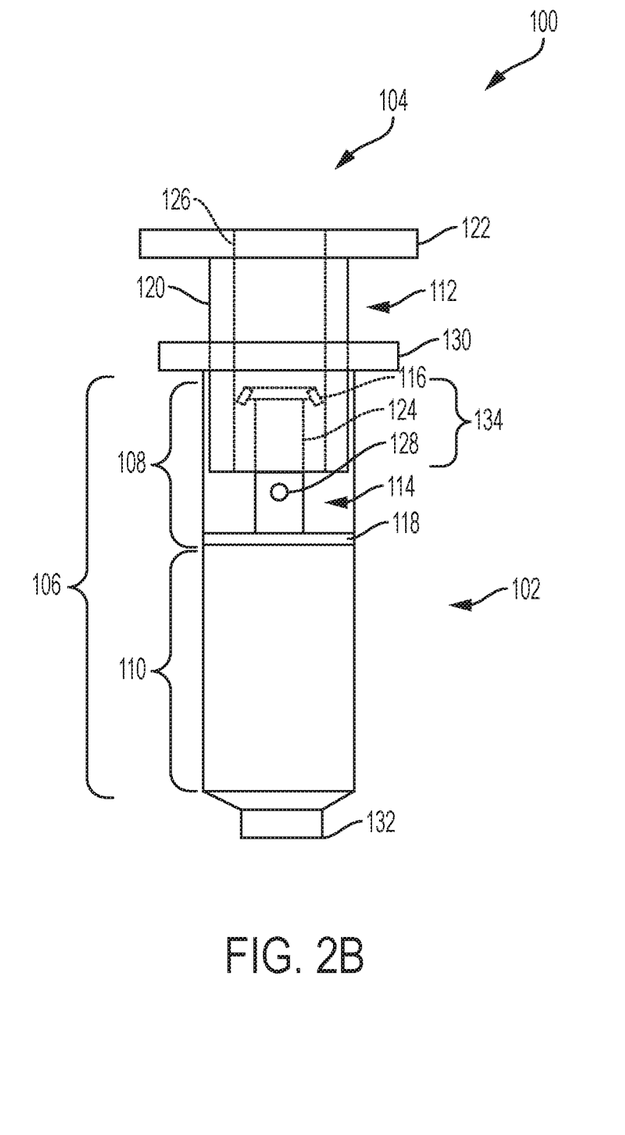

FIGS. 2A-2B are diagrams showing perspective and side views, respectively, of the example syringe 100 of FIGS. 1A-1B after mechanical failure in the contact portion 116 of the plunger member 104. In the example shown, the contact portion 116 permits the top portion 112 to move independently of the bottom portion 114 when a stress in the contact portion—e.g., due to a force applied to the plunger flange 122 by an operator and an opposing force applied to the seal 118 by a viscous fluid in the second inner volume portion 110—exceeds a critical stress. When this happens, the contact portion 116 mechanically fails as shown in FIGS. 2A-2B, and the top portion 112 extends into the inner chamber 106 without exerting a force upon the bottom portion 114. In the example shown, this causes the top portion 112 to overlap a portion of the bottom portion 114 as shown by the overlap region 134 in FIGS. 2A-2B. In the example shown, the bottom portion 114 is longer than the top portion 112. Accordingly, after mechanical failure in the contact portion 116, the top portion 112 cannot cause the bottom portion 114 to move and further dispense fluid from the outlet 132.

In the example shown, the top portion 112 includes a tubular portion 120 and the plunger flange 122. The bottom portion 114 includes a cylindrical portion 124 between the contact portion 116 and the seal 118, and the diameter of the cylindrical portion 124 is less than the inner diameter of the tubular portion 120. In some implementations, however (e.g., as shown in FIGS. 3B, 3D, and 3F), the bottom portion 114 is generally tubular, the top portion 112 includes a cylindrical portion between its first and second ends, and the diameter of the cylindrical portion is less than the inner diameter of the bottom portion 114. Such configurations may allow for the top portion 112 to extend into the inner chamber 106 (e.g., the second end of the top portion 112 extending past the first end of the bottom portion) after failure of the contact portion 116. In the example shown, the length of the bottom portion 114 is greater than the length of the top portion 112 so that the second end of the top portion 112 cannot apply force to the seal 118 after the contact portion 116 has mechanically failed (since the plunger flange 122 will contact the barrel flange 130 before the second end of the top portion 112 makes contact with the seal 118).

In the example shown, the top portion 112 defines an opening 126. The opening 126 is configured to allow fluid flow between the first inner volume portion 108 an exterior of the top portion 112 after mechanical failure in the contact portion 116. Furthermore, in the example shown, the bottom portion 114 also defines an opening 128 that is configured to allow fluid flow between the first inner volume portion 108 and the opening 126 after mechanical failure in the contact portion 116. Accordingly, when top portion 112 extends into the first inner volume portion 108 after mechanical failure in the contact portion 116, air in the first inner volume portion 108 may be expelled from the syringe 100, preventing pressure from being applied to the bottom portion 116 (which could allow further dispensing of a fluid in the second inner volume portion 110 from the outlet 132).

FIGS. 3A-3F are diagrams showing side views of example plunger members 302 for use in a syringe. Each of the example plunger members 302 includes a top portion 304, a bottom portion 306, and a contact portion 308, and may be used in a syringe as described herein. For example, any of the example plunger members 302 may be used in place of plunger member 104 in the syringe 100 of FIGS. 1A-1B and 2A-2B. In the examples shown, the length of each top portion 304 is less than the length of the corresponding bottom portion 306.

Figure 3A:
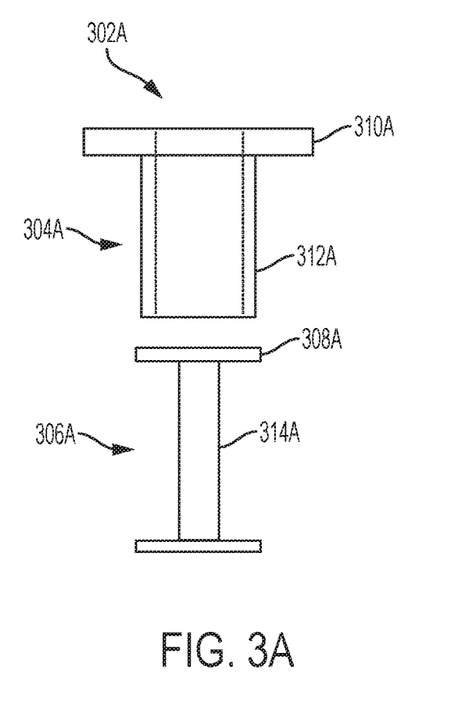
FIGS. 3A-3F are diagrams showing side views of example plunger members for use in a syringe.
Figure 3B:
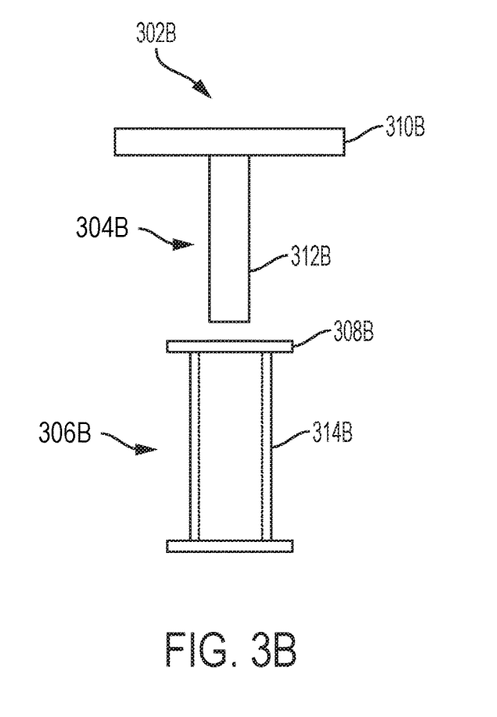
Figure 3C:
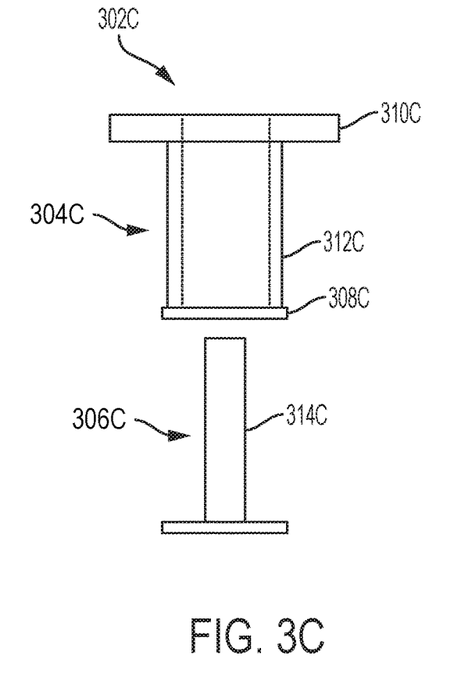
Figure 3D:
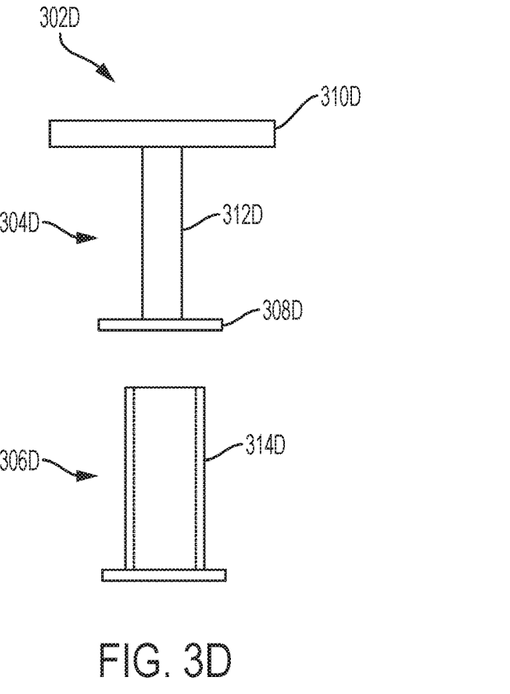
Figure 3E:
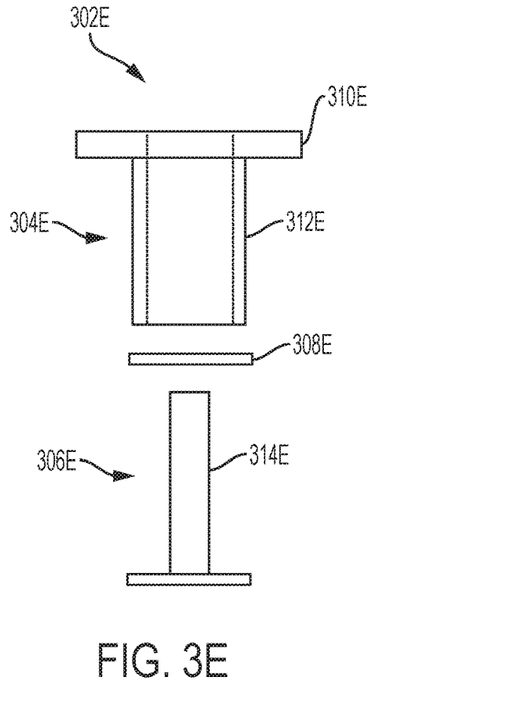
Figure 3F:
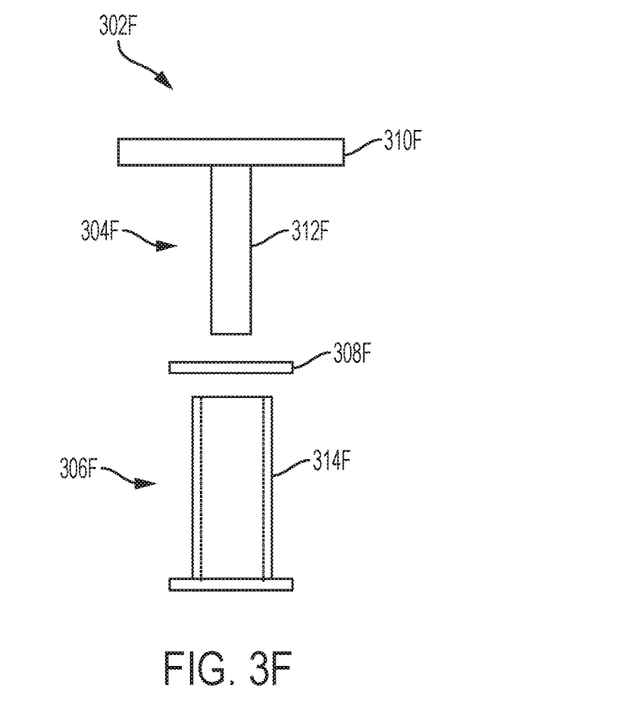

The example plunger member 302A of FIG. 3A includes a top portion 304A with a flange 310A and a tubular portion 312A, a bottom portion 306A with a cylindrical portion 314A, and a contact portion 308A that is integral with the bottom portion 306A. In the example shown, the inner diameter of the tubular portion 312A is greater than the diameter of the cylindrical portion 314A. During normal operation, a force may be applied to the flange 310A, and the force may be transferred from the top portion 304A to the bottom portion 306A through the contact portion 308A. The contact portion 308A may experience a stress in response to the force applied to the flange 310A (e.g., caused by a force differential between the force applied to the flange 310A and an opposing force applied to the bottom portion 306A, such as, for example, by a viscous fluid in a syringe). If the stress in the contact portion 308A exceeds a critical stress, the contact portion 308A may mechanically fail (e.g., sever, split, tear, or rupture) and allow the tubular portion 312A to extend past the cylindrical portion 314A, preventing the force applied to the flange 310A from being transferred to the bottom portion 306A.

The example plunger member 302B of FIG. 3B includes a top portion 304B with a flange 310B and a cylindrical portion 312B, a bottom portion 306B with a tubular portion 314B, and a contact portion 308B that is integral with the bottom portion 306B. In the example shown, the inner diameter of the tubular portion 314B is greater than the diameter of the cylindrical portion 312B. During normal operation, a force may be applied to the flange 310B, and the force may be transferred from the top portion 304B to the bottom portion 306B through the contact portion 308B. The contact portion 308B may experience a stress in response to the force applied to the flange 310B (e.g., caused by a force differential between the force applied to the flange 310B and an opposing force applied to the bottom portion 306B, such as, for example, by a viscous fluid in a syringe). If the stress in the contact portion 308B exceeds a critical stress, the contact portion 308B may mechanically fail (e.g., sever, split, tear, or rupture) and allow the cylindrical portion 312B to extend into the inner diameter of the tubular portion 314B, preventing the force applied to the flange 310B from being transferred to the bottom portion 306B.

The example plunger member 302C of FIG. 3C includes a top portion 304C with a flange 310C and a tubular portion 312C, a bottom portion 306C with a cylindrical portion 314C, and a contact portion 308C that is integral with the top portion 304C. In the example shown, the inner diameter of the tubular portion 312C is greater than the diameter of the cylindrical portion 314C. During normal operation, a force may be applied to the flange 310C, and the force may be transferred from the top portion 304C to the bottom portion 306C through the contact portion 308C. The contact portion 308C may experience a stress in response to the force applied to the flange 310C (e.g., caused by a force differential between the force applied to the flange 310C and an opposing force applied to the bottom portion 306C, such as, for example, by a viscous fluid in a syringe). If the stress in the contact portion 308C exceeds a critical stress, the contact portion 308C may mechanically fail (e.g., sever, split, tear, or rupture) and allow the tubular portion 312C to extend past the cylindrical portion 314C, preventing the force applied to the flange 310C from being transferred to the bottom portion 306C.

The example plunger member 302D of FIG. 3D includes a top portion 304D with a flange 310D and a cylindrical portion 312D, a bottom portion 306D with a tubular portion 314D, and a contact portion 308D that is integral with the top portion 304D. In the example shown, the inner diameter of the tubular portion 314D is greater than the diameter of the cylindrical portion 312D. During normal operation, a force may be applied to the flange 310D, and the force may be transferred from the top portion 304D to the bottom portion 306D through the contact portion 308D. The contact portion 308D may experience a stress in response to the force applied to the flange 310D (e.g., caused by a force differential between the force applied to the flange 310D and an opposing force applied to the bottom portion 306D, such as, for example, by a viscous fluid in a syringe). If the stress in the contact portion 308D exceeds a critical stress, the contact portion 308D may mechanically fail (e.g., sever, split, tear, or rupture) and allow the cylindrical portion 312D to extend into the inner diameter of the tubular portion 314D, preventing the force applied to the flange 310D from being transferred to the bottom portion 306D.

The example plunger member 302E of FIG. 3E includes a top portion 304E with a flange 310E and a tubular portion 312E, a bottom portion 306E with a cylindrical portion 314E, and a contact portion 308E that is distinct from the top portion 304E and the bottom portion 306E. In the example shown, the inner diameter of the tubular portion 312E is greater than the diameter of the cylindrical portion 314E. During normal operation, a force may be applied to the flange 310E, and the force may be transferred from the top portion 304E to the bottom portion 306E through the contact portion 308E. The contact portion 308E may experience a stress in response to the force applied to the flange 310E (e.g., caused by a force differential between the force applied to the flange 310E and an opposing force applied to the bottom portion 306E, such as, for example, by a viscous fluid in a syringe). If the stress in the contact portion 308E exceeds a critical stress, the contact portion 308E may mechanically fail (e.g., sever, split, tear, or rupture) and allow the tubular portion 314E to extend past the cylindrical portion 314E, preventing the force applied to the flange 310E from being transferred to the bottom portion 306E.

The example plunger member 302F of FIG. 3F includes a top portion 304F with a flange 310F and a cylindrical portion 312F, a bottom portion 306F with a tubular portion 314F, and a contact portion 308F that is distinct from the top portion 304F and the bottom portion 306F. In the example shown, the inner diameter of the tubular portion 314F is greater than the diameter of the cylindrical portion 312f. During normal operation, a force may be applied to the flange 310F, and the force may be transferred from the top portion 304F to the bottom portion 306F through the contact portion 308F. The contact portion 308F may experience a stress in response to the force applied to the flange 310F (e.g., caused by a force differential between the force applied to the flange 310F and an opposing force applied to the bottom portion 306F, such as, for example, by a viscous fluid in a syringe). If the stress in the contact portion 308F exceeds a critical stress, the contact portion 308F may mechanically fail (e.g., sever, split, tear, or rupture) and allow the cylindrical portion 312F to extend into the inner diameter of the tubular portion 314F, preventing the force applied to the flange 310F from being transferred to the bottom portion 306F.

FIGS. 4A-4C are diagrams showing perspective views of example contact portion configurations for plunger members 402. Each of the example plunger members 402 includes a top portion 404, a bottom portion 406, and a contact portion 308, and may be used in a syringe as described herein. For instance, any of the example plunger members 402 may be used in place of plunger member 104 in the syringe 100 of FIGS. 1A-1B and 2A-2B.

The example plunger member 402A of FIG. 4A includes a tubular top portion 404A, a cylindrical bottom portion 406A, and a contact portion 408A that is integral with the bottom portion 406A. In the example shown, the inner diameter of the top portion 404A is greater than the diameter of the bottom portion 406A, and the contact portion 408A is a solid membrane. The membrane may be configured to mechanically fail upon experiencing a stress greater than a pre-determined critical stress. In some instances, the membrane is designed with a particular thickness that is based upon the yield strength of the composition material.

The example plunger member 402B of FIG. 4B includes a tubular top portion 404B, a cylindrical bottom portion 406B, and a contact portion 408B that is integral with the top portion 404B. In the example shown, the inner diameter of the top portion 404B is greater than the diameter of the bottom portion 406B, and the contact portion 408A is a membrane with perforations 410. The perforations 410 of the contact portion 408B may be configured to mechanically fail upon experiencing a stress greater than a pre-determined critical stress (e.g., a stress greater than ten (10) Newtons (N)), for example.

The example plunger member 402C of FIG. 4C includes a tubular top portion 404C, a cylindrical bottom portion 406C, and a contact portion 408C that includes multiple connecting members 412 coupled between the top portion 404C and the bottom portion 406C. In the example shown, the inner diameter of the top portion 404C is greater than the diameter of the bottom portion 406C. The connecting member 412 may be configured to mechanically fail upon experiencing a stress greater than a pre-determined critical stress. For example, the connecting members 412 may be cylindrical and designed with a particular diameter that is based upon the yield strength of the composition material. The connecting members 412 may be configured to mechanically fail upon experiencing a stress greater than ten (10) Newtons (N), for example.

Figure 5:
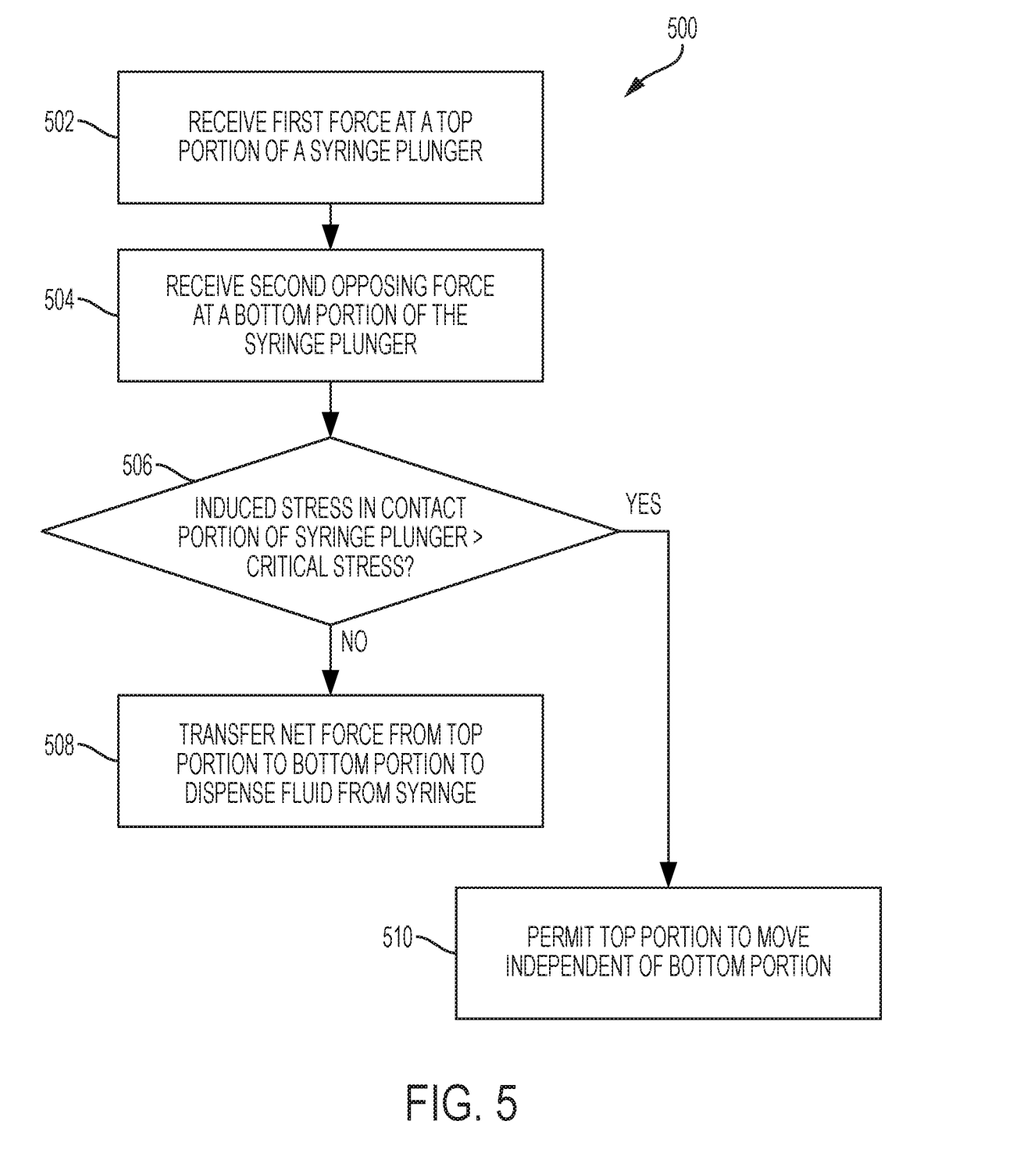
FIG. 5 is a flow diagram showing an example process for operating a syringe.

FIG. 5 is a flow diagram showing an example process 500 for operating a syringe. The process 500 may be used to operate a syringe according to the present disclosure. For example, the process 500 may be used to operate the syringe 100 of FIGS. 1A-1B and 2A-2B or another type of syringe that includes a contact portion configured to mechanically fail upon experiencing a stress that exceeds a critical stress.

At 502, a top portion of a syringe plunger receives a first force. The first force may be applied by an operator to a flange of the syringe plunger, or to another portion of the syringe plunger. The top portion of the syringe plunger may be coupled to a bottom portion of the syringe plunger via a contact portion. The first force may be co-axial or substantially co-axial with the plunger and barrel of the syringe. For example, referring to the example syringe 100 of FIGS. 1A-1B, the first force may be applied to the plunger flange 122 by an operator in a direction toward the barrel member 102 (the downward direction when referring to FIGS. 1B and 2B), and may be co-axial with the plunger member 104 and the barrel member 102.

At 504, the bottom portion of the syringe plunger receives a second force from a fluid in the barrel of the syringe. The second force may be in response to the first force and opposite the first force received at 502. The second force may be due to the viscosity of the fluid, a force caused by pressure in the fluid at an outlet of the barrel of the syringe, friction between the plunger and the barrel of the syringe, or a combination thereof. For example, referring again to the example syringe 100 of FIGS. 1A-1B, the second force may be applied to the seal 118 by a fluid in the second inner volume portion 110 of the barrel member 102 (the upward direction when referring to FIGS. 1B and 2B), and may be co-axial with the plunger member 104 and the barrel member 102.

At 506, a stress is induced in a contact portion of the syringe plunger. The stress may be a tension, compression, or other type of stress incident upon the contact portion, and may be caused by the first force received at 502 and the second force received at 504. For example, referring again to the example syringe 100 of FIGS. 1A-1B, the first and second forces may act upon the contact portion 116 of the plunger member 104 and cause a tension in the contact portion 116. In some implementations, however, the first and second forces may cause a compression or another type of stress in the contact portion 116. The stress in the contact portion may also be caused by other internal forces acting inside the syringe as well.

If the stress received at 506 is not greater than a critical stress, then the process proceeds to 508, where the net force of the first and second forces in the co-axial direction is transferred to a fluid in the syringe (e.g., to dispense the fluid from the syringe). Referring again to the example syringe 100 of FIGS. 1A-1B, the top portion 112 may transfer a force (the net of the first and second forces) to the bottom portion 114 through the contact portion 116, which in turn transfers the force to a fluid in the second inner volume portion 110 of the syringe 100 to dispense the fluid from the outlet 132.

If, however, the stress received at 506 is greater than the critical stress, then the process proceeds to 510, where the top portion of the plunger member is permitted to move independent of the bottom portion of the plunger member. For example, in some implementations, an end of the top portion may be permitted to extend past an end of the bottom portion (e.g., as shown in FIGS. 2A-2B). The top portion may be permitted to move independent of the bottom portion due to a mechanical failure in the contact portion of the syringe plunger. For example, referring to the example syringe 100 of FIGS. 2A-2B, the contact portion 116 may break in response to a stress induced therein being greater than the critical stress, and may accordingly allow the lower end of the top portion 112 to extend past the upper end of the bottom portion 114, and into the first inner volume portion 108 of the inner chamber 106. When this happens, the force applied to the top portion 112 may be prevented from being transferred to the bottom portion 114, preventing any fluid in the second inner volume portion 110 from being dispensed from the outlet 132.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

A number of embodiments have been described. Nevertheless, it will be understood that various modifications can be made. Accordingly, other embodiments are within the scope of the following claims.

What is claimed is:

1. A syringe comprising:
a barrel member that defines an inner chamber; and
a plunger member sized to fit within the barrel member, the plunger member comprising:
a contact portion;
a top portion comprising a first end and a second end opposite the first end, the first end of the top portion adapted to receive a first force co-axial with the barrel member during operation, the second end of the top portion in contact with the contact portion;
a bottom portion comprising a first end and a second end opposite the first end, the bottom portion having a length greater than or equal to a length of the top portion, the first end of the bottom portion in contact with the contact portion, the second end of the bottom portion dividing the inner chamber of the barrel member into a first inner volume portion and a second inner volume portion;
wherein the contact portion permits the top portion to move independent of the bottom portion in response to a stress in the contact portion exceeding a critical stress, the stress in the contact portion based on the first force applied to the first end of the top portion and a second force opposite the first force, the second force applied to the second end of the bottom portion by a fluid in the second inner volume portion of the inner chamber;
wherein the top portion defines an opening configured to allow fluid flow between the first inner volume portion and an exterior of the top portion.

2. The syringe of claim 1, wherein the contact portion permits the top portion to extend into the first inner volume portion without exerting a force upon the bottom portion in response to a stress in the contact portion exceeding the critical stress.

3. The syringe of claim 1, wherein the top portion comprises a tubular portion between the first end and the second end, the bottom portion comprises a cylindrical portion between the first end and the second end, and a diameter of the cylindrical portion of the bottom portion is less than an inner diameter of the tubular portion of the top portion.

4. The syringe of claim 1, wherein the contact portion is configured to mechanically fail when the stress exceeds the critical stress.

5. The syringe of claim 4, wherein the critical stress is based upon the yield strength of the contact portion.

6. The syringe of claim 1, wherein the critical stress is between ten (10) and one hundred (100) Newtons.

7. The syringe of claim 1, wherein the contact portion is integral with the top portion.

8. The syringe of claim 1, wherein the contact portion is integral with the bottom portion.

9. The syringe of claim 1, wherein the contact portion comprises perforations.

10. The syringe of claim 1, wherein the contact portion comprises multiple connecting members coupled between the top portion and the bottom portion.

11. A syringe comprising:
a barrel member that defines an inner chamber; and
a plunger member sized to fit within the barrel member, the plunger member comprising:
a contact portion;
a top portion comprising a first end and a second end opposite the first end, the first end of the top portion adapted to receive a first force co-axial with the barrel member during operation, the second end of the top portion in contact with the contact portion;
a bottom portion comprising a first end and a second end opposite the first end, the bottom portion having a length greater than or equal to a length of the top portion, the first end of the bottom portion in contact with the contact portion, the second end of the bottom portion dividing the inner chamber of the barrel member into a first inner volume portion and a second inner volume portion;

wherein the contact portion permits the top portion to move independent of the bottom portion in response to a stress in the contact portion exceeding a critical stress, the stress in the contact portion based on the first force applied to the first end of the top portion and a second force opposite the first force, the second force applied to the second end of the bottom portion by a fluid in the second inner volume portion of the inner chamber;

wherein the bottom portion comprises a tubular portion between the first end and the second end, the top portion comprises a cylindrical portion between the first end and the second end, and a diameter of the cylindrical portion of the top portion is less than an inner diameter of the tubular portion of the bottom portion.

12. The syringe of claim 11, wherein the contact portion permits the top portion to extend into the first inner volume portion without exerting a force upon the bottom portion in response to a stress in the contact portion exceeding the critical stress.

13. The syringe of claim 11, wherein the contact portion is configured to mechanically fail when the stress exceeds the critical stress.

14. The syringe of claim 13, wherein the critical stress is based upon the yield strength of the contact portion.

15. The syringe of claim 11, wherein the contact portion is integral with the top portion.

16. The syringe of claim 11, wherein the contact portion is integral with the bottom portion.

17. The syringe of claim 11, wherein the contact portion comprises perforations.

18. The syringe of claim 11, wherein the contact portion comprises multiple connecting members coupled between the top portion and the bottom portion.

19. A syringe comprising:
a barrel member that defines an inner chamber; and
a plunger member sized to fit within the barrel member, the plunger member comprising:
a contact portion;
a top portion comprising a first end and a second end opposite the first end, the first end of the top portion adapted to receive a first force co-axial with the barrel member during operation, the second end of the top portion in contact with the contact portion;
a bottom portion comprising a first end and a second end opposite the first end, the bottom portion having a length greater than or equal to a length of the top portion, the first end of the bottom portion in contact with the contact portion, the second end of the bottom portion dividing the inner chamber of the barrel member into a first inner volume portion and a second inner volume portion;
wherein the contact portion permits the top portion to move independent of the bottom portion in response to a stress in the contact portion exceeding a critical stress, the stress in the contact portion based on the first force applied to the first end of the top portion and a second force opposite the first force, the second force applied to the second end of the bottom portion by a fluid in the second inner volume portion of the inner chamber;
wherein the top portion defines a first opening and the bottom portion defines a second opening configured to allow fluid flow between the first inner volume portion and the opening of the top portion.

* * * * *